United States Patent [19]
Molina et al.

[11] Patent Number: 6,027,693
[45] Date of Patent: Feb. 22, 2000

[54] SEALED REPLACEABLE SENSOR

[75] Inventors: Joe G. Molina, El Paso, Tex.; Jack David Rodesiler, West Chicago, Ill.

[73] Assignee: BRK Brands, Inc., Aurora, Ill.

[21] Appl. No.: 08/845,614

[22] Filed: Apr. 25, 1997

[51] Int. Cl.[7] .................................................. G01N 27/00
[52] U.S. Cl. ...................... 422/98; 73/31.02; 73/31.05; 204/403; 204/431; 340/628; 340/632; 422/83; 429/96
[58] Field of Search ..................... 422/83, 98; 73/31.01, 73/31.02, 31.05; 204/400, 403, 431; 340/628–630, 632–634; 429/96, 99

[56] References Cited

U.S. PATENT DOCUMENTS

| | | |
|---|---|---|
| 4,238,679 | 12/1980 | Macmillan et al. . |
| 4,525,704 | 6/1985 | Campbell et al. . |
| 4,540,980 | 9/1985 | Porco . |
| 4,608,556 | 8/1986 | Cole . |
| 5,063,164 | 11/1991 | Goldstein ................................ 436/169 |
| 5,280,273 | 1/1994 | Goldstein . |
| 5,420,440 | 5/1995 | Ketler et al. . |
| 5,661,244 | 8/1997 | Nishimura et al. . |
| 5,694,932 | 12/1997 | Michel . |
| 5,793,295 | 8/1998 | Goldstein . |

*Primary Examiner*—Jan Ludlow
*Attorney, Agent, or Firm*—Rockey, Milnamow & Katz, Ltd.

[57] ABSTRACT

A gas detector having a sealed sensor assembly is only exposed to the ambient atmosphere when the detector is to be placed in the service. The detector is placed in the service by removing an elongated planar adhesive backed sealing member. The gas sensor also incorporates a replaceable biomemetic sensing material which is carried within a housing within the detector. The housing contains an internal region wherein the gas sensing material is located. The internal region is sealed where the housing is attached to a printed circuit board on one hand and by the removable sealing planar member on the other hand so as to protect the gas sensitive material from contamination or exposure to the atmosphere until the unit is placed into service.

4 Claims, 3 Drawing Sheets

SEALED REPLACEABLE SENSOR

FIELD OF THE INVENTION

The invention pertains to ambient condition detectors. More particularly, the invention pertains to gas detectors alone or in combination with other types of detectors.

BACKGROUND OF THE INVENTION

Ambient condition detectors are known and are useful devices in providing a warning of a dangerous ambient condition. Representative ambient conditions include smoke, fire, heat or temperature, and gas such as carbon monoxide.

With respect to gas detectors, a variety of different types of gas sensors are known. Some of these are solid state devices, others are electrochemical devices. Another class includes biomimetic-type materials of a type disclosed in U.S. Pat. No. 5,063,164.

Materials of the above-noted type change opacity in the presence of a selected gas such as carbon monoxide. Sensors which incorporate such materials can be used to detect the presence of carbon monoxide in a region being supervised wherein the gas is present at levels and for time intervals long enough to be dangerous.

Such material perform best when installed if care is taken during manufacturer to insure that the gas sensitive materials are not exposed prematurely to either the gas or other contaminants. There thus is a need in such sensors for seals which are effective to prevent premature exposure of the material to the ambient atmosphere.

SUMMARY OF THE INVENTION

A sealed ambient condition detector incorporates a housing with an internal region. Within the housing is carried a sealed, removable gas sensing element. The gas sensing element is sealed from the ambient atmosphere until the detector is ready for use.

The gas sensing element in one aspect can be covered with a removable planar sealing member. Additionally, apertures provided on the housing for electrical connections to and from the gas sensing element can be sealed by means of a plastic, rubberized or elasto-metric sealing material in the form of a gasket.

Numerous other advantages and features of the present invention will become readily apparent from the following detailed description of the invention and the embodiments thereof, from the claims and from the accompanying drawings.

BRIEF DESCRIPTION OF THE INVENTION

DETAILED DESCRIPTION OF THE PREFERRED EMBODIMENTS

Figure 1:
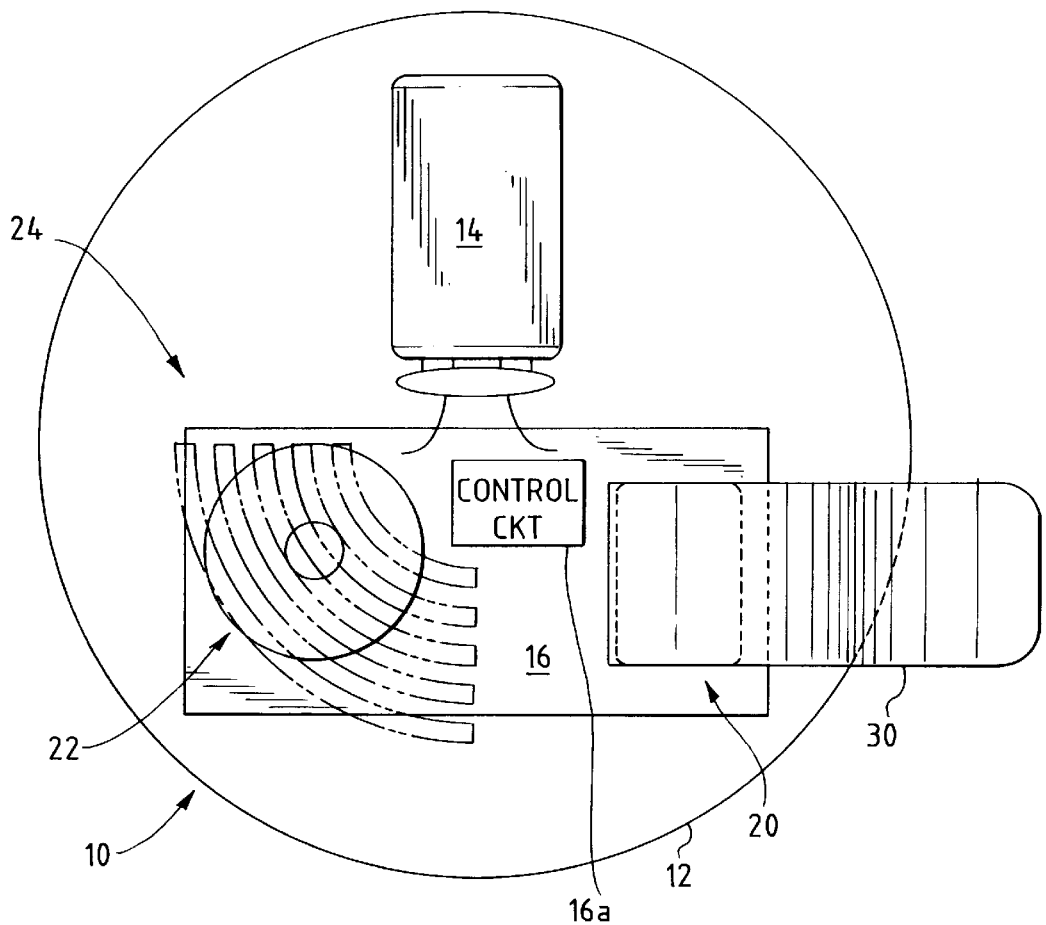
FIG. 1 is a top plan, partly schematic view of a detector incorporating a sealed gas sensor.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 1 illustrates a detector 10 which could be a gas sensor, such as a carbon monoxide detector alone or a gas sensor in combination with another form of an ambient condition sensor such as smoke or temperature. The detector 10 includes a housing 12 which carries a source of electrical energy, a replaceable battery 14.

The housing 12 also carries a printed circuit board 16 to which the battery 14 is connected. The printed circuit board 16 supports a gas sensor indicated generally at 20 and a smoke sensor, which could be an ionization-type smoke sensor indicated generally at 22. Apertures 24 permit the ingress and egress of ambient atmosphere including smoke and/or gas into the housing 12. Alternately, element 22 can be a horn or other type of audible alarm device.

Figure 2:
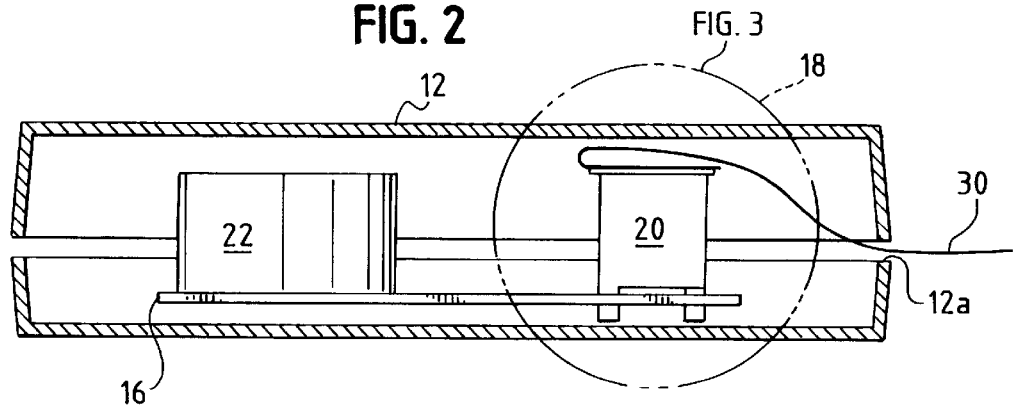
FIG. 2 is a side elevational view, partly in section, of the detector of FIG. 1.

The sensor 20 is sealed by a removable planar sealing member 30 which extends from a slot 12a in the housing 12 (best seen in FIG. 2). The member 30 is attached to the sensor 20 by an adhesive layer.

When installed, the detector 10 is activated by inserting the battery 14 to energize the unit. The removable planar member 30 is pulled from the sensor 20 thereby exposing the gas sensor 20 to the adjacent ambient atmosphere.

Figure 3:
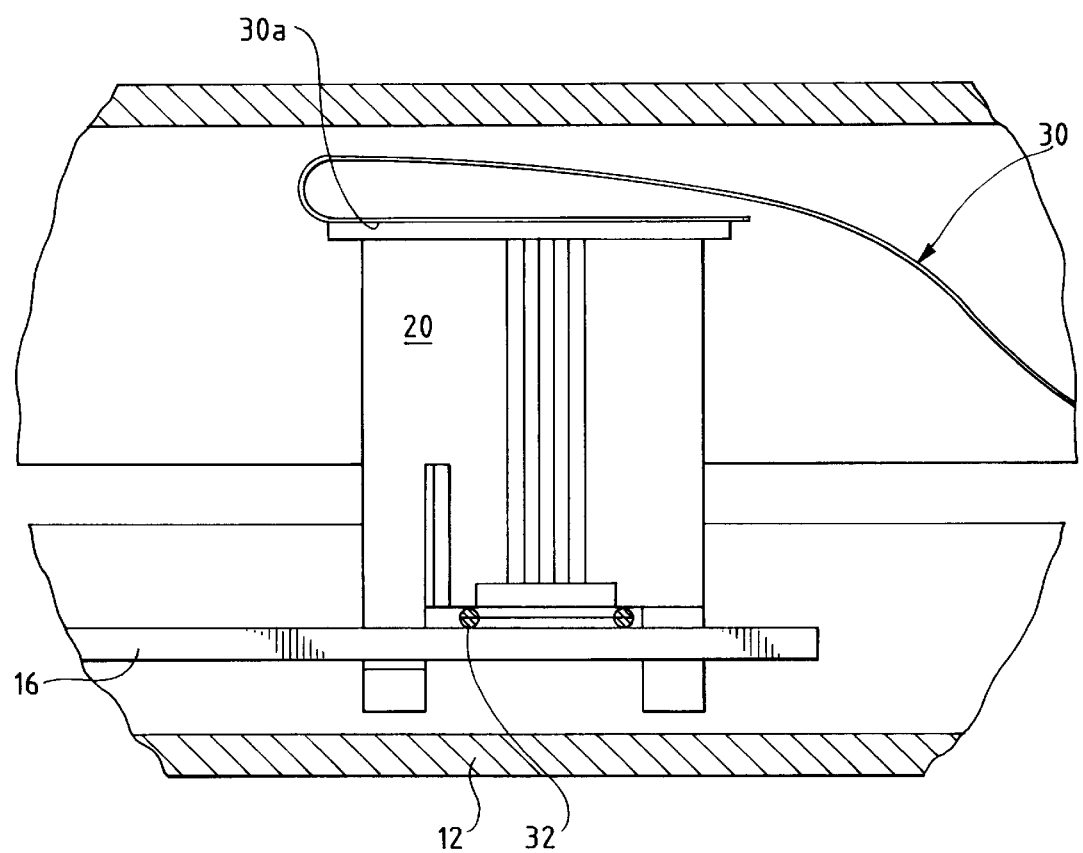
FIG. 3 is an enlarged side elevational view of a portion of FIG. 2.

FIG. 3 is an enlarged partial view of the detector 10 illustrating in more detail a region 18 indicated in FIG. 2. As is illustrated in FIG. 3, the sensor 20 is mounted on the printed circuit board 16, for example via a snap-fit.

The removable planar member 30 has an adhesive backing 30a. The member 30 can be peeled off of the sensor 20 by pulling on it. Once the member 30 has been removed, the sensor 20 will be exposed to the concentration of gas, such as carbon monoxide in the ambient atmosphere.

Figure 4:
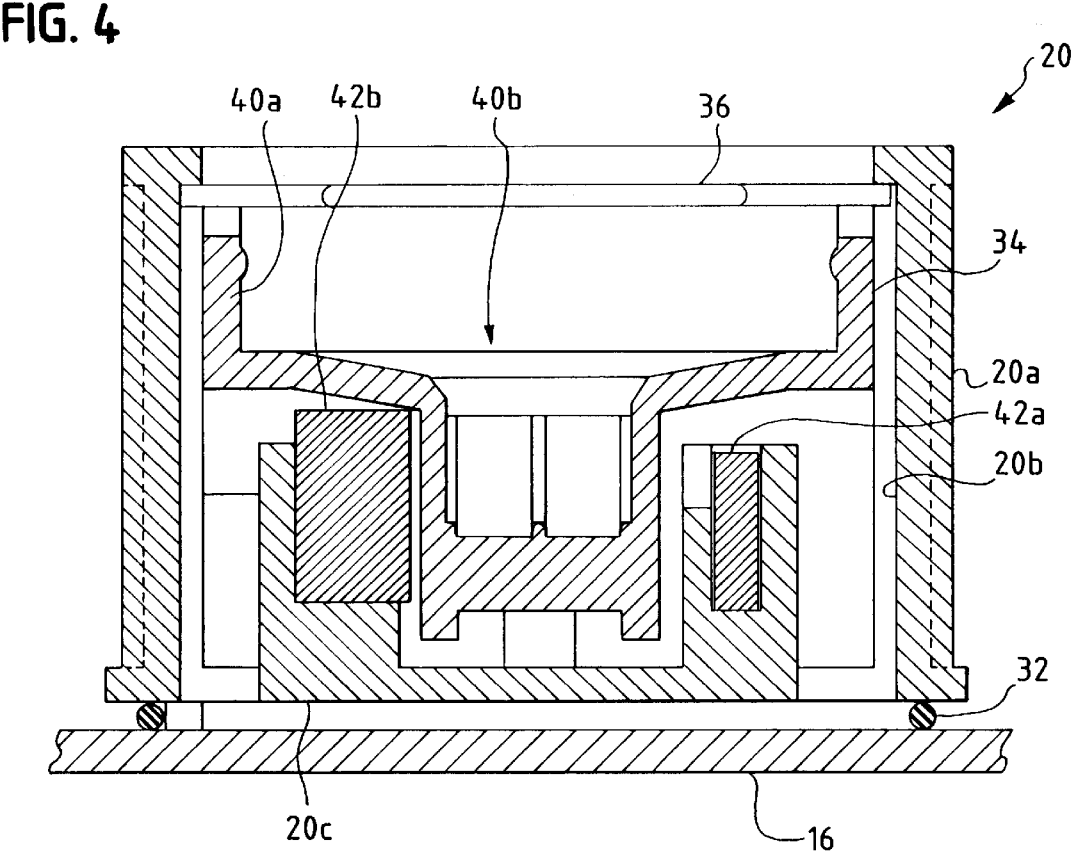
FIG. 4 is an enlarged side sectional view of the sensor of FIG. 3.

The sensor 20 is formed with a housing 20a which defines an interior volume 20b (best seen in FIG. 4). In addition to the adhesive backed flexible, removable top seal 30, the sensor 20 is also sealed, when affixed to the PC board 16 by a gasket 32. The gasket 32 can be in a variety of shapes and formed of a variety of resilient sealing materials without departing from the spirit and scope of the present invention. Gasket materials could include silicone, rubberized materials or other forms of resilient deformable sealing materials without departing from the spirit and scope of the present invention.

As is illustrated in more detail in FIG. 4, the sensor 20 carries a biomimetic sensor assembly 34 which is removably supported within the region 20b via the housing 20a.

The sensor assembly 34 is retained without the housing 20a by a wire retaining clip 36. The sensor assembly 34 includes a supporting frame 40a which carries biomimetic sensing material 40b. For replacement purposes, the frame 40a and associated sensing material 40b can be removed from the housing 20a after the retaining clip 36 has been removed. A new sensor assembly can be reinserted into the housing 20a.

The housing 20a also carries electrical components which include a source of radiant energy indicated generally at 42a and a displaced sensor of radiant energy 42b. The source 42a is energized either continuously or intermittently.

Radiant energy is projected through the material 40b to the detector 42b. As the material changes in response to ambient gas conditions, such as CO, the level of radiant energy received at the sensor 42 changes indicative of the level induration of the ambient gas. Electrical signals from the receiver or sensor 42d can be detected by control circuitry 16a mounted on the printed circuit board 16.

In response to detected signals from the sensor 42b, the control circuitry 16a can cause the detector 10 to go into alarm and admit an audible alarm.

It should be noted that as an alternate to the unit 22 functioning as a smoke detector, an audible alarm unit can be mounted at that point. In the event that the detector 10 incorporates a smoke detector and a gas detector, an audible alarm unit would be mounted elsewhere on the unit.

Figure 5:
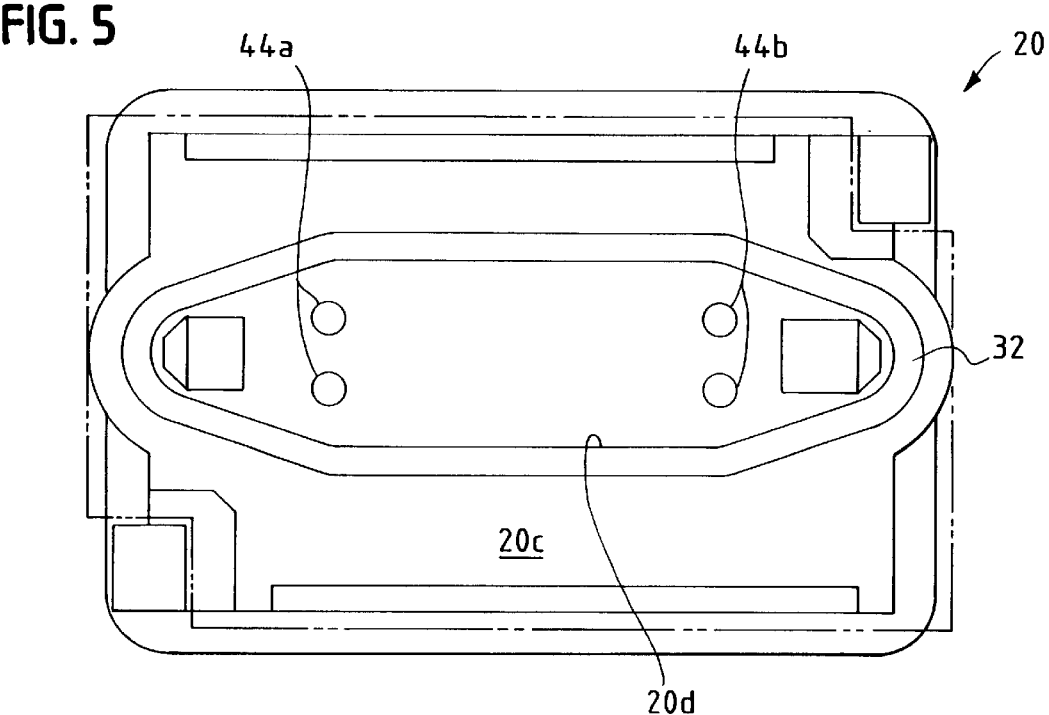
FIG. 5 is a bottom plan view of the sensor of FIG. 3.

FIG. 5 is a view of the sensor 20 looking toward surface 20c thereof which is oriented toward printed circuit board 16. The surface 20c defines an aperture 20d around which the gasket 32 forms a seal.

Electrical connections, such as the connections 44a and 44b can be made to the electrical components 42a, 42b in the region 20b within a totally sealed region of the sensor 20. Hence, the sensor 20 when assembled onto the printed circuit board with the removable sealing member 30 carried thereon represents a totally sealed sensor. Only when the detector 10 is installed and ready for use is the sensor material 40b exposed to the ambient atmosphere by removing the sealing layer 30. It would also be understood that if and when the sensor assembly 34 is replaced, another sealing layer 30a can be applied to the sensor 20 to reseal that unit. Hence, the replacement sensor assembly can be resealed until the detector is ready to be put back into service.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A detector, comprising:

a detector housing having an enclosing wall which defines an interior volume and which has apertures through said wall to admit ambient air into the interior volume;

a sensor housing carried within said detector housing interior volume, the sensor housing having an element retaining region and an aperture opening the element retaining region into the detector housing interior volume;

a sensing element insertable into said retaining region;

a planar, flexible sealing member sealed to said sensor housing to cover said aperture which precludes interaction between the sensing element and adjacent ambient atmosphere conditions until the sealing member is peeled from said sensor housing;

an alarm indicating device carried within said detector housing;

a printed circuit board carried within said detector housing, wherein said sensor housing is mounted on said printed circuit board, and wherein said sensing element is electrically connected to said printed circuit board, said printed circuit board, having control circuitry for the detector;

said detector housing enclosing wall including a slot, wherein said planar, flexible sealing member extends from said sensor housing through said slot of said detector housing for gripping outside said detector housing by a user to remove said planar flexible sealing member from said sensor housing;

a battery electrically connected to said printed circuit board and to said alarm indicating device; and a gasket arranged between said sensor housing and said printed circuit board for sealing the sensor housing to the printed circuit board.

2. A detector according to claim 1 wherein said sensing element comprises a biomimetic sensor.

3. A detector according to claim 1 further comprising a smoke detector element carried within said detector housing.

4. A detector according to claim 1 wherein said sensing element comprises a frame supporting a biomimetic sensing material, said frame removably held within said element retaining region.

* * * * *